US006221847B1

(12) United States Patent
Barefoot et al.

(10) Patent No.: US 6,221,847 B1
(45) Date of Patent: Apr. 24, 2001

(54) COMPOSITION AND METHOD FOR TREATING BACTERIAL INFECTION

(75) Inventors: Susan F. Barefoot, Liberty, SC (US); Priya Ratnam, San Ramon, CA (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 09/313,752

(22) Filed: May 27, 1999

Related U.S. Application Data

(63) Continuation-in-part of application No. 08/928,450, filed on Sep. 12, 1997, now Pat. No. 5,981,473.
(60) Provisional application No. 60/026,036, filed on Sep. 13, 1996.

(51) Int. Cl.[7] .............................. A61K 38/00; C12N 1/20; C12P 1/00
(52) U.S. Cl. ................................. 514/21; 514/2; 435/42; 435/170; 435/252.1; 435/252.9; 435/253.4
(58) Field of Search ........................... 514/2, 21; 435/42, 435/170, 252.1, 252.9, 253.4

(56) References Cited

U.S. PATENT DOCUMENTS

| 4,133,887 | 1/1979 | Sherlock ................................ 424/266 |
| 4,138,488 | 2/1979 | Sherlock et al. ...................... 424/250 |
| 4,139,625 | 2/1979 | Sherlock ................................ 424/266 |
| 4,143,141 | 3/1979 | Ensminger et al. ................... 424/253 |
| 4,183,924 | 1/1980 | Green et al. .......................... 424/242 |
| 4,213,978 | 7/1980 | Bodor et al. ......................... 424/241 |
| 4,255,418 | 3/1981 | Bailey .................................. 424/145 |
| 4,299,826 | 11/1981 | Luedders .............................. 424/181 |
| 4,335,115 | 6/1982 | Thompson ........................... 424/181 |
| 4,486,448 | 12/1984 | Ser et al. .............................. 424/294 |
| 4,514,385 | 4/1985 | Damani et al. ........................ 424/81 |
| 4,536,399 | 8/1985 | Flynn et al. ........................... 514/63 |
| 4,800,197 | 1/1989 | Kowcz et al. ........................ 514/162 |
| 5,096,718 | 3/1992 | Ayres et al. ............................... 426/9 |
| 5,260,292 | 11/1993 | Robinson et al. .................... 514/198 |
| 5,334,582 | 8/1994 | Blackburn et al. ....................... 514/2 |
| 5,409,917 | 4/1995 | Robinson et al. .................... 514/200 |
| 5,411,742 | 5/1995 | Sebag et al. .......................... 424/450 |
| 5,443,844 | 8/1995 | McDaniel ............................ 424/484 |
| 5,446,028 | 8/1995 | Klein et al. ............................. 514/43 |
| 5,449,519 | 9/1995 | Wolf et al. ............................ 424/401 |
| 5,453,276 | 9/1995 | Nakatsu et al. ...................... 424/405 |
| 5,639,659 | 6/1997 | Barefoot et al. ................... 435/252.1 |
| 5,981,473 | * 11/1999 | Barefoot et al. ......................... 514/2 |

FOREIGN PATENT DOCUMENTS

| 002049835 | 1/1990 | (JP) . |
| 002049836 | 1/1992 | (JP) . |
| 002049833 | 9/1996 | (JP) . |
| 002049834 | 5/1997 | (JP) . |
| WO8912399 | 12/1989 | (WO) . |
| WO9632482 | 10/1996 | (WO) . |

OTHER PUBLICATIONS

Ratnam et al., *Lait* (1999) pp. 125–136, Partial purification and characterization of the bacteriocin produced by *Propionibacterium jensenii* B1264.

Pulverer et al., *Zbl. Bakt. Hyg., I. Abt.Orig.A*, (1978) pp. 325–327, Propionicins, Bacteriocins Produced by Propionibacterium avidum Propionizine–durch Propionibakterien erzeugte Bakeriozine.

* cited by examiner

*Primary Examiner*—Bennett Celsa
(74) *Attorney, Agent, or Firm*—Dority & Manning, P.A.

(57) ABSTRACT

A method and composition for preventing and treating infection from clinically relevant bacterial isolates is disclosed. The composition contains an anti-bacterial agent that inhibits the growth of the bacteria, including members of both gram negative and gram positive isolates. In particular, the anti-bacterial agent comprises a bacteriocin produced by Propionibacterium. For instance, in one embodiment, the bacteriocin is produced by the B1264 strain of *Propionibacterium jensenii*.

23 Claims, No Drawings

COMPOSITION AND METHOD FOR TREATING BACTERIAL INFECTION

The present Application is a Continuation-in-Part Application based on a U.S. patent application Ser. No. 08/928,450, filed Sep. 12, 1997 now U.S. Pat. No. 5,981,473 and claiming priority from Provisional Application Ser. No. 60/026,036, filed Sep. 13, 1996.

FIELD OF THE INVENTION

The present invention is generally directed to a composition and method for treating bacterial infections. More particularly, the present invention is directed to the use of a protein produced by bacteria from dairy or classical propionibacteria that inhibits the growth of bacteria that cause acne. Additionally, the bacteriocin of the present invention has been shown to be effective at inhibiting or killing a number of different gram-positive and gram-negative bacterial isolates which cause clinical infection in human and animal patients.

BACKGROUND OF THE INVENTION

Acne (formally known as "acne vulgaris") is a skin disease which afflicts, in some form, approximately 80 to 90 percent of all teenagers. Acne can also affect many adults and infants. The severity of acne can range from minor skin lesions called comedones to nodules and cysts which can potentially permanently scar skin tissue.

The areas of the body that are commonly affected by acne are the face, chest and upper back. These areas of the body have a high sebaceous gland concentration which causes the skin to be oily.

Acne is believed to start with increased release of hormones in the body such as androgens. Young adults going through puberty, for instance, tend to produce more hormones such as androgens. It is believed that androgens stimulate the sebaceous glands to produce more sebum, which is an oily substance released on the skin. Sebum is a lipid-laden product comprised of a mixture of fats, waxes and fatty materials.

As more and more is produced, sebum can agglomerate and form solid plugs known as comedones in the hair follicles. Formation of a comedone, in turn, causes layers of dead skin known as keratin to accumulate and be retained within the lining of the follicles. The buildup of keratin causes hyperkeratosis of the follicular opening, which can completely close off the follicular canal.

Within the follicular canal are bacteria indigenous to the follicular lining. Included in the bacteria are anaerobic, gram positive organisms classified for instance as *Propionibacterium acnes* or *Propionibacterium granulosum*. When comedones form in the follicular opening, these bacteria feed on the sebum. Specifically, the bacteria produce lipases that hydrolyze triglycerides and release free fatty acids. The fatty acids thus generated in combination with the bacteria activate the immune system of the body causing inflammation, swelling and redness around the follicle. Depending upon the degree of inflammation, pustules, cysts, nodules, and papules may form.

In the past, many different treatments have been proposed for curing acne. Such treatments include topical keratolytic agents, topical or systematic antibiotics, or hormonal treatments designed to limit sebum secretion. Unfortunately, some of these treatments can produce adverse side affects. Topical keratolytic agents include, for instance, tretinoin and benzoyl peroxide. These anti-acne agents prevent the blockage of follicular canals and reopen clogged follicular openings by breaking down keratin. Some keratolytic agents, however, can irritate the skin causing excessive dryness, scaling, swelling, burning, peeling, redness and allergic reactions.

Antibiotics that have been used in the past to treat acne include tetracycline, erythromycin, clindamycin, meclocyclin, metronidazole, minocycline and doxycycline. While administration of these drugs is often effective in treating acne, antibiotics have several disadvantages. For example, when taken orally, antibiotics may cause many undesirable side effects including abdominal cramps, black tongue, fatigue, depression, nausea, and other various effects. When applied topically, the antibiotics can lose their effectiveness if used for a prolonged period of time due to resistance developed by the bacteria.

The hormones estrogen and antiandrogens have also been used to treat acne in severe cases. These hormones when taken orally, however, can feminize adolescent males and can increase the risk of blood clots and cancers. Thus, hormones are rarely administered orally.

In view of the disadvantages associated with current acne treatments, a need exists for an acne preventive agent that does not create any of the above adverse side effects. A need also exists for an anti-acne agent that destroys the bacteria that causes the inflammation associated with acne.

SUMMARY OF THE INVENTION

The present invention recognizes and addresses the foregoing disadvantages, and others of prior art constructions and methods.

In summary, the present invention is generally directed to an anti-bacterial protein referred to as a bacteriocin, that can be used to destroy and inhibit the growth of the bacteria that are responsible for the inflammatory symptoms associated with acne. In addition to its usefulness as a treatment for acne, the bacteriocin of the present invention is also useful as a broad spectrum antibiotic, and has been shown to effectively inhibit the growth of, or kill, a variety of clinically relevant bacteria, including both gram-positive and gram negative bacterial isolates.

As used herein, the term "clinically relevant" bacteria refers to bacterial isolates responsible for causing significant morbidity and mortality in human and animal patients. Among such isolates are a number of members of the Enterobacteriaceae family. For example, *Escherichia coli* is a gram negative organism which is a major cause of watery or bloody diarrhea. Additionally, *E. coli* infection is a common cause of bacteremia and meningitis in newborns. Other members of the Enterobacteriaceae family which are associated with significant morbidity include *Proteus vulgaris, Enterobacter aerogenes, Shigella flexneri* and *Serratia marcescens*.

According to the present invention, the bacteriocin is produced by a bacteria from the genus Propionibacterium and particularly from the classical or dairy strains. For instance, in one embodiment, the bacteriocins can be produced from *Propionibacterium jensenii,* and more particularly by the B1264 strain of *Propionibacterium jensenii*. It has been discovered that these bacteriocins not only can be used to treat acne and other bacterial infections but are stable across a pH range and at relatively high temperatures. This stability coupled with the fact that the bacteriocin is produced by a food related organism, makes the bacteriocin of the present invention a highly effective and desirous agent for treating acne and other clinically relevant bacterial infections.

Bacteriocins produced by *Propionibacterium jensenii* are discussed in U.S. Pat. No. 5,639,659 which is incorporated herein by reference in its entirety. In the prior application, the bacteriocins were used primarily to inhibit the growth of bacteria cultures of *Lactobacillus bulgaricus* and *Streptococcus thermophilus* in order to control the pH of a food product, such as yogurt. It was not disclosed nor was it apparent in that application, however, that the bacteriocins may also be used to inhibit the bacteria associated with acne and other medical ailments.

Accordingly, it is an object of the present invention to provide a method and a composition for treating acne.

Another object of the present invention is to provide a method and composition for treating acne that involves the use of bacteriocins produced from one or more strains of bacteria classified in the genus Propionibacterium.

Another object of the present invention is to provide a composition containing bacteriocins produced by *Propionibacterium jensenii* that destroy and inhibit the growth of bacteria associated with acne.

It is another object of the present invention to provide a topical preparation for treating acne that contains bacteriocins produced by *Propionibacterium jensenii*.

Still another object of the present invention is to provide a method for destroying and inhibiting the growth of *Propionibacterium acnes* and *Propionibacterium granulosum* using a bacteriocin produced by *Propionibacterium jensenii*.

It is still another object of the present invention to provide a method for destroying and inhibiting the growth of clinically relevant gram negative and gram positive bacterial isolates using a bacteriocin produced by *Propionibacterium jensenii*.

It is yet another object of the present invention to provide a method for treating bacterial infection, caused by both gram positive and gram negative bacterial isolates, by administering a therapeutically active dosage of a composition containing a bacteriocin produced by *Propionibacterium jensenii*.

It is still a further object of the present invention to provide a broad spectrum antibiotic composition containing a bacteriocin produced by *Propionibacterium jensenii* useful for treating gram negative and gram positive bacterial infections.

These and other objects of the present invention are achieved by providing a process for treating acne. The process includes the step of treating an infected area of the body with an effective amount of bacteriocins produced by a species of Propionibacterium, such as *Propionibacterium jensenii*, to destroy cutaneous bacteria responsible for causing acne and other diseases. Specifically, the bacteriocins are capable of inhibiting the growth of acne bacteria such as *Propionibacterium acnes* and *Propionibacterium granulosum*. In one embodiment, bacteriocins produced by the B1264 strain of *Propionibacterium jensenii* are used. The B-1264 strain of *Propionibacterium jensenii* was deposited with the American Type Culture Collection having an address of 10801 University Boulevard, Manassas, Va. 20110-2209 on Apr. 20, 2000.

In addition to its usefulness as a treatment for acne, the bacteriocin of the present invention is also useful as a broad spectrum antibiotic and has been shown to substantially inhibit the growth of, or kill, a variety of clinically relevant bacteria, including both gram-positive and gram negative bacterial isolates.

As used herein, the terms "gram positive" and "gram negative" refer to a method of classifying bacteria based upon their differential staining characteristics when stained with a Gram stain. Some species of bacteria have a cell wall consisting primarily of a thick layer of peptidoglycan. Other species have a much thinner layer of peptidoglycan and an outer, as well as an inner, membrane. When bacteria are subjected to a Gram stain, differential staining of the bacteria results from differences in the bacterial cell wall structure. Bacteria classified as gram positive appear purple when examined under a light microscope, while those classified as gram-negative appear reddish.

The bacteriocins of the present invention may be used to treat acne or other types of infection caused by susceptible gram negative or gram positive bacterial isolates. Besides containing the bacteriocin produced by *Propionibacterium jensenii*, the composition can contain other antimicrobial agents, wetting agents, carriers, emulsifying agents and the like, depending upon the type of administration and the preparation desired. The composition can contain all, or a mixture of some, of the above ingredients as desired.

In particular, the bacteriocins are believed to be well suited for use with keratolytic agents such as benzoyl peroxide, retinoic acid and salicylic acid. When applied to the skin, the bacteriocins are preferably combined in a topical composition. However, one of skill in the art will recognize that a pharmaceutical composition containing the *Propionibacterium jensenii* bacteriocin can be administered in various dosages and by various techniques well-known to those in the medical or veterinary arts, taking into consideration such factors as the age, sex, weight, species and condition of the particular patient, and the route of administration.

For example, the composition of the present invention can be administered via a percutaneous route, via mucosal administration (e.g., oral, nasal, anal, vaginal), or via a parenteral route (intradermal, intramuscular, subcutaneous, intravenous, or intraperitoneal). The *Propionibacterium jensenii* bacteriocin composition can be administered alone, or can be co-administered or sequentially administered with other treatments or therapy. Other forms of administration may include suspensions, syrups or elixirs, and preparations for parenteral, subcutaneous, intradermal, intramuscular, or intravenous administration (e.g., injectable administration), such as sterile suspensions or emulsions. The parenteral bacteriocin composition may be administered in admixture with a suitable carrier, diluent, or excipient such as sterile water, physiological saline, glucose, dextrose, or the like. The composition can contain auxiliary substances such as wetting or emulsifying agents, pH buffering agents, adjuvants, gelling, or viscosity enhancing additives, preservatives, flavoring agents, colors, and the like, depending upon the route of administration and the preparation desired. Standard pharmaceutical textbooks, such as "REMINGTON'S PHARMACEUTICAL SCIENCE," 17th Edition, 1985, may be consulted to prepare suitable preparations, without undue experimentation.

The bacteriocin of the present invention is administered in a therapeutically effective dosage to treat bacterial infection caused by susceptible gram negative or gram positive organisms. As used herein, the term "therapeutically effective dosage" means a dosage which can kill, or inhibit the growth of, clinically relevant bacteria such that the numbers of bacteria decrease to a level at which clinical signs and symptoms associated with the infection are ameliorated.

As is well known to one of skill in the art, the therapeutically effective dosage and route of administration useful for treating bacterial infections are determined by the therapeutic range and nature of the bacteriocin composition, and by other known factors such as the age, weight and condition of the patient. Screening procedures, such as the $LD_{50}$ assay, known to those in the art can be used to determine effective dosages and routes of administration without undue experimentation. In general, it is believed therapeutically effective dosages can range from about a few hundred micrograms per kilogram of body weight per day to about a few grams per kilogram of body weight per day.

Other objects, features and aspects of the present invention are discussed in greater detail below.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to a composition and method for treating acne and other bacterial infections. In particular, a bacteriocin produced by dairy propionibacteria, such as *Propionibacterium jensenii*, is used to destroy and inhibit the growth of susceptible gram negative and gram positive bacteria that cause clinically relevant infections in human and animal patients. Specifically, it has been discovered that the bacteriocins of the present invention inhibit the growth of *Propionibacterium acnes* and *Propionibacterium granulosum*, which are cutaneous bacteria present in the follicular canal of the skin. Additionally, it has been shown that the *Propionibacterium jensenii* bacteriocin inhibits a variety of other clinically relevant bacterial isolates, including *Staphylococcus aureus, Escherichia coli, Shigella sonnei, Shigella flexneri, Serratia marcescens,* and *Listeria monocytogenes.*

In order to treat acne, the bacteriocins produced by dairy propionibacteria are applied topically in the infected area. As will be described in more detail hereinafter, the bacteriocins can be combined with various ingredients to form a topical composition. Once applied to the skin, the composition destroys the bacteria associated with acne reducing inflammation and infection.

Besides acne, the bacteriocins of the present invention can be used to treat other medical ailments and diseases resulting from infection with clinically relevant bacterial isolates. Specifically, the bacteriocins can be used to treat infection caused by any susceptible gram negative or gram positive bacteria isolate. For example, it is believed that the bacteriocins of the present invention can also be used to treat endocarditis, brain abscesses, dental infections, conjunctivitis, pulmonary infections, and peritonitis.

A bacteriocin is an anti-bacterial agent comprising a protein or a complex of proteins. The bacteriocins for use in the present invention are derived from bacteria cultures of propionibacteria, such as the classical or dairy species of Propionibacterium. The classical or dairy species include *Propionibacterium jensenii, P. acidipropionici, P. freudenreichii* subspecies *freudenreichii* and *shermanii*, and *P. thoenii*. These classical species are extremely useful organisms in the food industry and are found in dairy fermentations, other natural fermentations such as silage and olives, and soil. During fermentative metabolism, they convert glucose and lactate to propionate, acetate, and carbon dioxide. The inhibitory effects of propionate and acetate are potentiated by the low pH encountered in Swiss cheese and other fermented products. Of particular advantage, the classical or dairy species of propionibacteria are food related bacteria that can be safely consumed in human food.

In one embodiment, bacteriocins produced by the 1264 strain of *Propionibacterium jensenii* have been found particularly well adapted for use in the process of the present invention. Besides being effective in inhibiting the growth of cutaneous bacteria cultures, bacteriocins produced by the B1264 strain of *Propionibacterium jensenii* are very stable. Through testing, it has been discovered that these bacteriocins can withstand temperatures of up to 100° C. for at least sixty minutes, remain active in a pH range from about 2 to about 10, are stable to solutions of sodium chloride, are stable in alcohols, are stable in up to 4M urea solutions and are stable in solutions of anionic detergent sodium dodecyl sulfate. Bacteriocins produced by the B1264 strain of *Propionibacterium jensenii* have a molecular size of between about 3,000 to about 10,000 Dalton.

Although it is believed that other strains of Propionibacterium, such as *Propionibacterium jensenii*, may produce bacteriocins that can be used in the present invention, it has been discovered that bacteriocins produced by the B1264 strain are particularly effective at inhibiting the growth of and destroying bacteria cultures believed to be responsible for many of the symptoms associated with acne and other diseases resulting from bacterial infection. These bacteriocins, for instance, have been found to be effective in destroying bacteria cultures of *Propionibacterium acnes* and *Propionibacterium granulosum*. More particularly, the bacteriocins have been found to inhibit the growth of *Propionibacterium acnes* ATCC 6919, *Propionibacterium acnes* ATCC 11827, and *Propionibacterium granulosum* ATCC 25564. It has also been observed that the bacteriocins inhibit *Propionibacterium avidum* ATCC 25577 and *Propionibacterium lymphophilum* ATCC 27520, which are strains of bacteria commonly present on the skin but not at the present time known to be associated with acne. Additionally, the bacteriocins of the present invention have been shown to inhibit a variety of gram negative and gram positive bacteria which cause clinical infections, including *Staphylococcus aureus, Enterobacter aerogenes, Escherichia coli, Shigella sonnei, Shigella flexneri, Salmonella typhimurium,* and *Listeria monocytogenes.*

It should be understood that the scope of the present invention is not to be limited to the use of bacteriocins produced by B1264 strain of *Propionibacterium jensenii*. The use of bacteriocins produced by the B1264 strain of *Propionibacterium jensenii* merely represents one embodiment of the present invention. It should be understood that the present invention is directed to the use of bacteriocins produced from any strain of Propionibacteria, and particularly to the classical or dairy strains. In a further alternative embodiment, it has also been discovered that bacteriocins produced by *Lactococcus lactis* subsp. *lactis* also inhibit cutaneous bacteria and thus can be used in the process of the present invention. As will be demonstrated in the examples to follow, provided herein is a simple screening test for determining whether a particular strain of Propionibacterium produces a bacteriocin that will inhibit the cutaneous bacteria responsible for causing acne.

In order to produce the bacteriocins, a particular culture of Propionibacterium is first grown in a suitable medium. As the bacteria grows, the bacteriocin of the present invention is produced. Once produced, the bacteriocin can be isolated and combined in a topical composition for application to the skin. It is believed that only a few molecules of the bacteriocin will be required to kill a cell of the targeted bacteria.

Alternatively, the Propionibacterium bacteriocin can be isolated and combined in a pharmaceutically effective dose in a composition for percutaneous, mucosal (e.g., oral, nasal, anal, vaginal), or parenteral intradermal, intramuscular, subcutaneous, intravenous, or intraperitoneal) administration.

In forming a topical preparation, the bacteriocins of the present invention can be combined with a wide variety of ingredients that can be added in order to facilitate application to the skin, to provide a benefit to the skin, or for some other benefit. For instance, the bacteriocins may be combined with other anti-acne agents, wetting agents, chelators, preservatives, or drying agents. For example, the bacteriocins of the present invention may be used in combination with all types of anti-acne agents that have anti-microbial properties and/or keratolytic properties. In particular, the bacteriocins may be used in combination with antibiotics. Of particular importance, however, it is believed that the bacteriocins would be well suited for use with compositions that will break down keratin such as salicylic acid, retinoic acid, and benzoyl peroxide. Benzoyl peroxide is also known to have some anti-microbial effect.

Wetting agents that may be used with the bacteriocins include quaternary ammonium compounds, sodium dodecyl sulfate, polyphosphates, carbopol, propylene glycol, polyethylene glycol, polyoxyethylenesorbitans, and mixtures thereof. Chelators can be included in the composition for binding with metal ions in order to facilitate the destruction of bacteria cells. Exemplary chelators that may be used in the present invention include EDTA, citric acid, and phosphoric acid. Linolenic acid may be also added to the composition in order to maintain the formulation of sebum in balance on the skin.

A parenteral antibiotic composition containing the *Propionibacterium jensenii* bacteriocin may be formulated as an admixture with a suitable carrier, diluent, or excipient such as sterile water, physiological saline, glucose, dextrose, or the like. Alternatively, the *Propionibacterium jensenii* bacteriocin may be delivered in a delivery system, such as a liposome or within other encapsulating agents. The bacteriocin composition can contain auxiliary substances such as emulsifying agents, pH buffering agents, gelling, or viscosity enhancing additives, flavoring agents, colors, and the like, depending upon the route of administration and the preparation desired.

The composition of the present invention may also contain adjuvants, such as aluminum hydroxide, muramyl dipeptide, and the like. Preservatives, such as benzoic acid, butylated hydroxy anisole (BHA) and parabens, and/or drying agents, such as alcohols, may also be added to the composition, if desired.

The present invention may be better understood with reference to the following examples.

EXAMPLE I

The following is one procedure that may be used in order to produce bacteriocins from Propionibacterium, such as *Propionibacterium jensenii,* and particularly from the B1264 strain of *Propionibacterium jensenii*.

*Propionibacterium jensenii* B1264, obtained from the Institute of Biochemistry and Physiology of Micro organisms; All Union Collection of Microorganisms at the Russian Academy of Sciences in Moscow (Accession No. VKM B-1264), from a 48 h culture was inoculated into sodium lactate broth (NLB) (0.1% inoculum) and held for 10 days at 32° C. under flowing $CO_2$ (0.4 L/min) to permit culture growth and bacteriocin production. The cells were removed from the cultures by centrifuging at 6,300×g for 30 min at 4° C. and filtering through a 0.45 μm pore-size filter.

The bacteriocins produced were precipitated by gradually adding ammonium sulfate (70% final concentration) to the filtered supernate with constant stirring. The mixture was held overnight at 4° C. The bacteriocins were agglomerated and formed into pellets by centrifuging at 19,600×g (30 min).

The pellets containing the bacteriocins were resuspended in 0.1 M sodium phosphate buffer (pH 6.4) at 5% original volume. Preparations to be examined for activity against *P. acnes* may be resuspended at 0.2% of original volume. The solution was dialyzed exhaustively against the same buffer at 4° C. using 3,500 molecular weight cut-off dialysis tubing. The dialysis removed salts and other low molecular weight components contained in the solution. The dialyzed preparation was then sterilized by passing it through a 0.45 μm pore-size filter resulting in a more concentrated crude bacteriocin preparation.

EXAMPLE II

The bacteriocins produced in Example I were then assayed against a reference culture of *Lactobacillus delbrueckii* subspecies *lactis*.

*Lactobacillus delbrueckii* subsp. *lactis* ATCC 4797 was grown overnight in Lactobacilli MRS broth at 37° C. Sufficient amounts of the culture were added to 5 ml soft MRS agar (Lactobacilli MRS broth containing 0.75% agar) to yield a final population of ≈$10^6$ cells per ml. The culture-soft MRS agar mixture was poured over the surface of sterile MRS agar (1.5% agar) plates.

Bacteriocins produced by *Propionibacterium jensenii* according to the procedure of Example I were diluted in serial two-fold dilutions. Dilutions were applied (in 10 μL portions) to the surface of the prepared plates. The plates were held at 37° C. under flowing $CO_2$ (0.4 L/h) for 16–18 hours and examined for zones of inhibition. It was observed that the bacteriocins inhibited the cultures of *L. delbrueckii* subsp. *lactis*. Titers were expressed as the reciprocal of the highest dilution inhibiting the indicator culture and are reported in activity units per milliliters.

Using the procedures described in Examples I and II, any strain of Propionibacterium, such as *Propionibacterium jensenii,* can be screened and tested for bacteriocin production. Once bacteriocins are found to exist, they can be easily tested against cutaneous propionibacteria as explained in the following Examples.

EXAMPLE III

The following represents one method for detecting bacteriocin inhibition against cutaneous propionibacteria contained in cultures. The method is referred to as the deferred agar spot assay modified appropriately for cutaneous propionibacteria and is particularly well adapted for use with bacteriocins produced by *Propionibacterium jensenii*.

Each pure culture of possible bacteriocin-producing propionibacteria (*Propionibacterium jensenii*) is grown at 32° C. for 48 h in sodium lactate broth (NLB). Each producer culture (10 μL) is then spot-inoculated to the center of sodium lactate agar (NLA) plates and held at 32° C. under flowing $CO_2$ for 8 days to permit bacteriocin production.

*Propionibacterium acnes, Propionibacterium granulosum* or other cutaneous propionibacteria to be examined for sensitivity to the bacteriocin are grown in actinomyces broth (Difco Laboratories, Detroit, Mich.) at 37° C. for 2 days under anaerobic conditions (BBL GasPak system). Plates containing possible bacteriocin-producing cultures are overlaid with 5 ml of soft actinomyces agar (actinomyces broth containing 0.75% agar) containing 15 μL of the culture being examined for sensitivity. To eliminate inhibition by $H_2O_2$ or organic acids, separate filter paper discs containing 15 μL of catalase and pronase E (20 mg/ml) are applied near the growth of the producer culture.

Plates are incubated anaerobically at 37° C. for 24–48 hours to permit growth of the culture being examined for sensitivity and are examined for zones of inhibition. Inhibition that is not affected by catalase and is sensitive to protease is considered to be due to a possible bacteriocin.

From the above procedure, it was discovered that bacteriocins produced by the B1264 strain of *Propionibacterium jensenii* inhibited the growth of bacteria cultures of *Propionibacterium acnes* ATCC 6919, *Propionibacterium acnes* ATCC 11827 and *Propionibacterium granulosum* ATCC 25564.

The above-described procedure may be used to screen any bacteriocin produced by *Propionibacterium jensenii* against any strain of cutaneous propionibacteria.

EXAMPLE IV

The following procedure is a method for detecting bacteriocin activity in solution against cutaneous propionibacteria. The method can be used for screening any bacteriocin produced by Propionibacterium. The following procedures include both the spot on lawn method and the critical dilution method.

*Propionibacterium acnes, Propionibacterium granulosum*, or other cutaneous propionibacteria to be examined for sensitivity to the bacteriocin are grown in actinomyces broth at 37° C. for 2 days under anaerobic conditions. Cultures (15 μL) being examined for sensitivity are added to soft actinomyces agar (5 ml) and the mixture is applied uniformly over each actinomyces agar plate. Preparations concentrated so as to contain 6,400 Activity Units/ml of bacteriocins are spotted (25 μl spots) onto the surface of the prepared plates. These plates are held at 37° C. for 2 days under anaerobic conditions to permit growth of the cutaneous culture and examined for zones of inhibition (lack of growth) where the bacteriocin was applied. Zones are evidence of bacteriocin inhibition.

This method can be modified to permit quantitation of bacteriocin activity against cutaneous cultures by preparing serial two-fold dilutions of bacteriocin solution and applying 25 μL spots from each dilution to the surface of the plates (containing cutaneous propionibacteria cultures in soft actinomyces agar). These plates are held at 37° C. for 2 days under anaerobic conditions to permit growth of the cutaneous culture and examined for zones of inhibition (lack of growth) where the bacteriocin was applied. Titers can be expressed as the reciprocal of the highest dilution inhibiting the indicator Propionibacterium culture and are reported in activity units (AU) per ml.

The above-procedure can be used to screen the effectiveness of any bacteriocins produced by Propionibacterium against any cutaneous propionibacteria.

EXAMPLE V

Bacteriocins produced by the B1264 strain of *Propionibacterium jensenii* were tested against cutaneous propionibacteria obtained from patients. Specifically, clinical specimens of open comedones or blackheads were obtained from fifteen patients. The comedones were homogenized and cultured on Marshall and Kelsey Medium as described in an article entitled: "Microbiology of Comedones in Acne Vulgaris" by Marples, et al., *J. Invest. Dermatol.*, Volume 60, Pages 80–83 (1973) and New Propionibacteria Isolation Medium as described in an article entitled: "New Medium for Isolating Propionibacteria and its Application to Assay of Normal Flora of Human Facial Skin" by Kishishita, et al., *Appl. Environ. Microbiol.*, Volume 40, Pages 1100–1105 (1980). 150 clinical cultures were isolated and identified by biochemical profiles and fatty acid analysis.

Bacteriocins produced by the B1264 strain of *Propionibacterium jensenii* were tested against the clinical isolates. The bacteriocins inhibited all 150 clinical isolates. Of the 150 isolates, 129 were identified as *Propionibacterium acnes* and the remaining 21 were identified as *Propionibacterium granulosum*.

EXAMPLE VI

Bacteriocins produced by the P126 strain of *Propionibacterium jensenii* were also tested against various cutaneous propionibacteria. It was observed that these bacteriocins did not inhibit the bacteria cultures although further testing may be needed to confirm these results. It is believed, however, that other strains of *Propionibacterium jensenii* will produce bacteriocins that may be used in the process of the present invention.

EXAMPLE VII

The following procedure was developed according to the present invention in order to further purify bacteriocins produced by Propionibacterium, especially bacteriocins produced by *Propionibacterium jensenii*.

A strong anion exchange resin, BIORAD MACRO-PREP Q (typically 6 milliliters packed wet volume), was prepared by washing 5 times with 0.025 M or 0.1 M sodium phosphate buffer (pH 6.0) containing 0.1% TWEEN 80, centrifuging at 6,300×g for 10 minutes, and decanting supernate. Crude bacteriocins produced by the B1264 strain of *Propionibacterium jensenii* as prepared in Example I (1.0 ml, 1600 AU/ml) were dialyzed for 24 h at 4° C. in 3500 MWCO tubing against 0.025 M sodium phosphate buffer (pH 6.0). The dialyzed bacteriocins were mixed with the washed resin, and held with gentle stirring for 10 minutes. Contaminating proteins, but not the bacteriocins, adsorbed to the resin. IEC-purified bacteriocins were recovered by decanting the supernate, repeatedly (5 to 6 times) washing the support with 1.0 ml of 0.025 M or 0.1 M sodium phosphate buffer (pH 6.0) containing 0.1% TWEEN 80 and combining the supernate and washings.

The above batch anion exchange chromatography procedure was found to yield 145% recovery of bacteriocin activity and a 22-fold increase in purification. Because of the increase in activity, it is believed that the above purification procedure may have removed some agents that were interfering with bacteriocin activity.

EXAMPLES VIII

The following three examples were performed in order to determine the stability of the bacteriocins produced by the B1264 strain of *Propionibacterium jensenii* when contained in various solvents. In one particular application of the present invention, the bacteriocins may be combined with an alcohol in producing a topical preparation. Thus, the following tests were performed in order to ensure that the bacteriocins would remain active in such preparations.

Crude bacteriocins produced by the B1264 strain of *Propionibacterium jensenii* as prepared in Example I were combined with methanol, ethanol and isopropanol and sterile deionized, distilled water to a final concentration of 0%, 15%, 30% and 50% (v/v). Each mixture was held at 18° C. to 22° C. for 0, 30, 60, 90 and 120 minutes and examined for activity against *L. delbrueckii* subsp. *lactis* ATCC 4797. Under the assay conditions, sodium phosphate buffer (0.1 M, pH 6.0) containing the same solvent concentrations did not inhibit the sensitive indicator culture. Therefore, mixtures were assayed directly for bacteriocin activity.

The following results were obtained:

TABLE 1

Effect of Solvents on Crude Bacteriocins

| | Activity (AU/ml) | | | | |
|---|---|---|---|---|---|
| Solvent | 0 min. | 30 min. | 60 min. | 90 min. | 120 min. |
| Methanol 0% | 1600 | 1600 | 1600 | 1600 | 1600 |
| Methanol 15% | 1600 | 1600 | 1600 | 1600 | 1600 |
| Methanol 30% | 3200 | 1600 | 1600 | 1600 | 1600 |
| Methanol 50% | 1600 | 1600 | 1600 | 1600 | 1600 |
| Ethanol 0% | 3200 | 3200 | 3200 | 3200 | 3200 |
| Ethanol 15% | 3200 | 3200 | 3200 | 3200 | 3200 |
| Ethanol 30% | 3200 | 1600 | 3200 | 3200 | 3200 |
| Ethanol 50% | 3200 | 3200 | 3200 | 3200 | 3200 |
| Isoprop 0% | 3200 | 3200 | 1600 | 1600 | 1600 |
| Isoprop 15% | 3200 | 3200 | 1600 | 1600 | 1600 |
| Isoprop 30% | 3200 | 1600 | 1600 | 1600 | 1600 |
| Isoprop 50% | 3200 | 3200 | 1600 | 1600 | 1600 |

Ethanol and isopropanol may possibly be used in a topical preparation containing the bacteriocins of the present invention for treating acne. As shown above, neither solvent had a dramatic effect upon the activity of the bacteriocins.

EXAMPLE IX

The same procedure described in Example VIII above was also carried out on bacteriocins produced by the B1264 strain of *Propionibacterium jensenii* that were partially purified by ion exchange chromatography as described in Example VII above. The following results were obtained:

TABLE 2

Effect of Solvents on IEC Purified Bacteriocins

| | Activity (AU/ml) | | | | |
|---|---|---|---|---|---|
| Solvent | 0 min. | 30 min. | 60 min. | 90 min. | 120 min. |
| Methanol 0% | 400 | 200 | 200 | 200 | 400 |
| Methanol 15% | 200 | 200 | 200 | 200 | 200 |
| Methanol 30% | 400 | 200 | 200 | 200 | 400 |
| Methanol 50% | 200 | 200 | 200 | 200 | 200 |
| Ethanol 0% | 400 | 400 | 200 | 200 | 400 |
| Ethanol 15% | 400 | 200 | 200 | 200 | 400 |
| Ethanol 30% | 400 | 200 | 200 | 200 | 200 |
| Ethanol 50% | 400 | 200 | 200 | 200 | 200 |
| Isoprop 0% | 400 | 200 | 200 | 200 | 400 |
| Isoprop 15% | 200 | 200 | 200 | 200 | 200 |
| Isoprop 30% | 100 | 100 | 100 | 100 | 100 |
| Isoprop 50% | 100 | 100 | 100 | 100 | 100 |

As shown above, none of the solvents had a dramatically adverse impact upon bacteriocin activity, further suggesting that the bacteriocins are well suited for use in topical preparations.

EXAMPLE X

The same procedure described in the Example VIII above was repeated except for the fact that the bacteriocins, instead of being examined for activity against *L. delbrueckii* subsp. *lactis,* were examined for activity against *Propionibacterium acnes* ATCC 6919. The following results were obtained:

TABLE 3

Effect of Solvents on Bacteriocins Assayed Against *P. Acne*

| | Activity (AU/ml) | | | | |
|---|---|---|---|---|---|
| Solvent | 0 min. | 30 min. | 60 min. | 90 min. | 120 min. |
| Methanol 0% | 400 | 400 | 400 | 400 | 200 |
| Methanol 15% | 400 | 200 | 200 | 400 | 400 |
| Methanol 30% | 400 | 400 | 400 | 400 | 400 |
| Methanol 50% | 400 | 200 | 200 | 400 | 400 |
| Ethanol 0% | 400 | 400 | 400 | 400 | 400 |
| Ethanol 15% | 400 | 400 | 200 | 200 | 400 |
| Ethanol 30% | 400 | 200 | 200 | 200 | 400 |
| Ethanol 50% | 400 | 200 | 200 | 200 | 200 |
| Isoprop 0% | 400 | 400 | 400 | 200 | 200 |
| Isoprop 15% | 400 | 400 | 400 | 200 | 200 |
| Isoprop 30% | 400 | 400 | 200 | 200 | 200 |
| Isoprop 50% | 100 | 100 | 100 | 100 | 100 |

As shown above, again, none of the solvents had a dramatically adverse impact upon bacteriocin activity, even when examined for activities against *Propionibacterium acnes.*

EXAMPLE XI

Besides bacteriocins produced by *Propionibacterium jensenii,* it was also discovered that bacteriocins produced by *Lactococcus lactis* subsp. *lactis* also inhibited cutaneous bacteria. These bacteriocins are commercially known as nisin or NISAPLIN.

Specifically, a solution of nisin containing 4,000 International Units per milliliter was tested for activity against *Propionibacterium acnes* ATCC 6919, *Propionibacterium acnes* ATCC 11827, *Propionibacterium avidum* ATCC 25577 and *Propionibacterium granulosum* ATCC 25564 according to the method described in Example IV above. It was observed that nisin inhibited all of the cutaneous cultures.

Nisin at a final concentration of 400 International Units per milliliter was also added to broth cultures of each of the above bacteria strains. The broth cultures were incubated anaerobically at 37° C. for 24 hours. It was observed that nisin markedly reduced the growth of each culture of cutaneous propionibacteria.

In view of these results, it is believed that nisin may also be used in the process of the present invention as an anti-acne agent or as an agent for treating other diseases caused by cutaneous bacteria.

EXAMPLE XII

In this study, the *Propionibacterium jensenii* B1264 bacteriocin ("*jenseniin P*") was assayed against various bacterial isolates to determine inhibitory effect.

To increase bacteriocin activity, *P. jensenii* B1264 cultures were incubated for a total of 14 days. Fermentation cultures were started by incubating 20 ml from a 44-hour broth culture of *P. jensenii* B1264, grown according to Example I, in 130 ml of modified sodium lactate broth (NLB) medium, containing 0.6% agar and 1.5% lactate syrup (Fisher Scientific Company, Pittsburgh, Pa.) in screwcapped 250 ml bottles. Bottles were incubated at 32° C. under flowing $CO_2$ (0.4 L/h) for 14 days with periodic agitation. Every 24 hours, for a total of 14 days, one bottle was removed from the incubator and the *jenseniin P* bacteriocin purified as described in Example I above, with minor modifications. Briefly, after 100 mmol/L NaCl was added to a 14-day culture of *P. jensenii* B1264, the culture was centrifuged at 17,400×g for 20 min. The supernatant was decanted; the pH of the supernatant reduced to approximately 2.5 and the supernatant centrifuged at 17,400×g for 25 min. The Jenseniin P bacteriocin was precipitated from the supernatant by the addition of ammonium sulfate (70% final concentration) and pelleted by centrifugation (17,400×g for 25 min.). The pellet was resuspended in 10 ml 0.1 M sodium phosphate buffer at pH 6.5 and concentrated to a volume of 2 ml in speed vacuum.

Activity of the bacteriocin purified from each time point was determined against the indicator culture *Lactobacillus delbrueckii* subsp. *lactis* ATCC 4797, as described in Example II above. Results showed that the bacteriocins purified from day 14 cultures exhibited the highest inhibition titers against the indicator organism, with the activity of the bacteriocin determined to be 12,800 Activity Units/ml against *L. delbrueckii* ATCC 4797.

Bacteriocin activity against a variety of gram negative and gram positive bacterial isolates was detected using a spot-on-lawn method and determined by a modification of the critical dilution assay as described in Examples III–V above. Briefly, several different bacterial pathogens were obtained from the Clemson University Food Microbiology Culture Collection (Dept. Food Science and Human Nutrition, Clemson, S.C.), propagated (1% inoculum) twice in brain heart infusion broth (BHI) and streaked for isolation prior to experimental use. Cultures were maintained in the appropriate growth medium containing 20% glycerol and stored at −70° C.

To assay the bacteriocin for the ability to inhibit different pathogens, cultures were grown at 37° C. for 16 h to 24 h, prior to preparing an indicator lawn from each culture by adjusting the $OD_{600}$ to 0.1, adding 100 μl of each culture to 5 ml of Brain Heart Infusion (BHI) soft agar, and applying the soft agar to prepoured agar plates. The Jenseniin P bacteriocin was spotted (20 μl) onto the surface of the resulting bacterial lawns. Plates were held at 37° C. for 24 h and examined for inhibition of the indicator lawn (D. A. Grinstead and S. F. Barefoot, 1992. Jenseniin G: A Heat Stable Bacteriocin Produced by *Propionibacterium jensenii* P126, *Appl Environ Microbiol* 58: 215–220 and Ratnam et al., 1999. Partial Purification and Characterization of the Bacteriocin Produced by *Propionibacterium jensenii* B 1264, *Lait* 79: 126–136; the contents of which are incorporated herein in their entirety). Results are as follows:

TABLE 4

Pathogens Assayed for Inhibition by Jenseniin P Bacteriocin

| Organism | Gram stain | Results |
| --- | --- | --- |
| *Enterobacter aerogenes* ATCC 13048 | negative | inhibited |
| *Escherichia coli* ATCC 25922 | negative | inhibited |
| *Listeria monocytogenes* | positive | inhibited |
| *L. murrayi* ATCC 25402 | positive | inhibited |
| *Pseudomonas aeruginosa* ATCC 3896 | negative | Not inhibited |

TABLE 4-continued

Pathogens Assayed for Inhibition by Jenseniin P Bacteriocin

| Organism | Gram stain | Results |
| --- | --- | --- |
| *Salmonella typhimurium* ATCC 14028 | negative | inhibited |
| *Serratia marcescens* ATCC 8100 | negative | inhibited |
| *Shigella flexneri* ATCC 12022 | negative | inhibited |
| *S. sonnei* ATCC 25931 | negative | inhibited |
| *Staphylococcus aureus* ATCC 25923 | positive | inhibited |
| *S. epidermidis* ATCC 1228 | positive | Not inhibited |
| *Streptococcus faecalis* ATCC 19433 | positive | Not inhibited |
| *S. pyrogenes* ATCC 19615 | positive | Not inhibited |
| *Proteus vulgaris* ATCC 13315 | negative | inhibited |
| *Bacillus cereus* ATCC 232 | positive | Not inhibited |
| *B. pumilus* ATCC 27142 | positive | inhibited |

It should be understood that the present invention is not limited to the specific bacteria or processes described herein and that any bacteriocin equivalent to those described falls within the scope of the present invention. Preparation routes of the bacteriocins and process steps of inhibiting bacteria are merely exemplary so as to enable one of ordinary skill in the art to produce the bacteriocin and use it according to the described process and its equivalents.

It will also be understood that although the form of the invention shown and described herein constitutes a preferred embodiment of the invention, it is not intended to illustrate all possible forms of the invention. In addition, it should be understood that aspects of the various embodiments may be interchanged both in whole or in part. The words used are the words of description rather that of limitation. Various changes and variations may be made to the present invention without departing from the spirit and scope of the invention.

What is claimed is:

1. A method for treating a bacterial infection in a patient comprising:
    administering to said patient a composition containing an anti-bacterial agent, said anti-bacterial agent comprising a bacteriocin produced by dairy propionibacteria selected from the group consisting of *Propionibacterium jensenii, P. acidipropionici, P. freudenreichii* subspecies *freudenreichii* and *shermanii, P. thoenii,* and combinations thereof, wherein said bacteriocin is administered in a therapeutically active dosage for a time effective to inhibit the growth of a bacterial isolate in said patient, said bacterial isolate comprising a member of the Enterobacteriaceae or a gram positive bacterium chosen from the group consisting of *Listeria moncytogenes, Staphylococcus aureus, Listeria murrayi,* and mixtures thereof.

2. A method according to claim 1, wherein said bacteriocin is produced by *Propionibacterium jensenii*.

3. A method according to claim 1, wherein said bacteriocin is produced by the B1264 strain of *Propionibacterium jensenii*.

4. A method according to claim 1, wherein said member of the Enterobacteriaceae is chosen from the group consisting of *Escheriachia coli, Proteus vulgaris, Enterobacter aerogenes, Shigella flexneri, Salmonella typhimurium, Serratia marcescens* and mixtures thereof.

5. A method according to claim 1, wherein said composition is administered via mucosal administration.

6. A method according to claim 1, wherein said composition is administered via parenteral administration.

7. A method according to claim 1, wherein said composition is administered within a delivery system.

8. A method according to claim 7, wherein said delivery system is a liposome.

9. A method according to claim 1, wherein said composition further comprises a pharmaceutically acceptable carrier.

10. A method according to claim 9, wherein said pharmaceutically acceptable carrier is chosen from the group consisting of physiological saline, dextrose, sterile water, and mixtures thereof.

11. A method according to claim 1, wherein said bacteriocin is administered in a therapeutically active dosage, for a time effective to kill the bacteria in said bacterial infection.

12. A method according to claim 11, wherein said therapeutically active dosage is in the range of about 100 μg per kilogram of body weight per minute to about 200 g per kilogram of body weight per minute.

13. A method for treating a bacterial infection in a patient comprising:

administering to said patient a composition containing an anti-bacterial agent, said anti-bacterial agent comprising a bacteriocin produced by *Propionibacterium jensenii*, wherein said bacteriocin is administered in a therapeutically active dosage for a time effective to inhibit the growth of a bacterial isolate in said patient, said bacterial isolate comprising a member of the Enterobacteriaceae or a gram positive bacterium chosen from the group consisting of *Listeria moncytogenes, Staphylococcus aureus, Listeria murrayi,* and mixtures thereof.

14. A method according to claim 13, wherein said bacteriocin is produced by the B1264 strain of *Propionibacterium jensenii.*

15. A method according to claim 13, wherein said member of the Enterobacteriaceae is chosen from the group consisting of *Escheriachia coli, Proteus vulgaris, Enterobacter aerogenes, Shigella flexneri, Salmonella typhimurium, Serratia marcescens* and mixtures thereof.

16. A method according to claim 13, wherein said composition is administered via mucosal administration.

17. A method according to claim 13, wherein said composition is administered via parenteral administration.

18. A method according to claim 13, wherein said composition is administered within a delivery system.

19. A method according to claim 18, wherein said delivery system is a liposome.

20. A method according to claim 13, wherein said composition further comprises a pharmaceutically acceptable carrier.

21. A method according to claim 20, wherein said pharmaceutically acceptable carrier is chosen from the group consisting of physiological saline, dextrose, sterile water, and mixtures thereof.

22. A method according to claim 13, wherein said bacteriocin is administered in a therapeutically active dosage, for a time effective to kill the bacteria in said bacterial infection.

23. A method according to claim 22, wherein said therapeutically active dosage is in the range of about 100 μg per kilogram of body weight per minute to about 200 g per kilogram of body weight per minute.

* * * * *